United States Patent [19]

Kukes et al.

[11] Patent Number: 4,522,936

[45] Date of Patent: Jun. 11, 1985

[54] METATHESIS CATALYST

[75] Inventors: Simon G. Kukes; Robert L. Banks, both of Bartlesville, Okla.

[73] Assignee: Phillips Petroleum Company, Bartlesville, Okla.

[21] Appl. No.: 611,785

[22] Filed: May 18, 1984

Related U.S. Application Data

[62] Division of Ser. No. 477,466, Mar. 21, 1983, Pat. No. 4,465,890.

[51] Int. Cl.$^3$ .......................... B01J 23/24; B01J 23/18
[52] U.S. Cl. ..................................... 502/249; 502/254; 502/305; 502/311; 502/322; 502/354
[58] Field of Search ............... 502/249, 254, 305, 311, 502/322, 354

[56] References Cited

U.S. PATENT DOCUMENTS

| | | | |
|---|---|---|---|
| Re. 28,593 | 10/1975 | Bethell et al. | 502/249 X |
| 3,365,513 | 1/1968 | Heckelsberg | 502/254 X |
| 3,677,933 | 7/1972 | Johnson et al. | 502/311 X |
| 3,691,100 | 9/1972 | Wright | 502/254 X |
| 3,926,856 | 12/1975 | Lussling et al. | 502/311 |
| 4,215,017 | 7/1980 | Reusser et al. | 502/254 X |
| 4,368,345 | 1/1983 | Dickinson | 502/254 X |
| 4,448,894 | 5/1984 | Hobbs | 502/249 |

Primary Examiner—Carl F. Dees

[57] ABSTRACT

A supported tungsten oxide or supported molybdenum oxide is treated with elemental tungsten, silicon or antimony. The composition is useful as a metathesis catalyst.

36 Claims, No Drawings

METATHESIS CATALYST

CROSS REFERENCES TO RELATED APPLICATIONS

The present application is a divisional application of application Ser. No. 477,466, now U.S. Pat. No. 4,465,890 entitled METATHESIS PROCESS AND CATALYST, filed Mar. 21, 1983 by the present inventors.

This invention relates to a novel composition of matter. In one aspect this invention relates to a metathesis catalyst. In another aspect this invention relates to the metathesis of olefinic and acetylenic compounds.

BACKGROUND

Olefin metathesis is one of the most recent catalyzed reactions of hydrocarbons to emerge. Discovered in 1959 this reaction opened up a new and exciting field of hydrocarbon chemistry and provided chemical routes for the interconversion of light olefinic hydrocarbons, the backbone of today's petrochemical industry, and for the synthesis of high-purity olefins for the specialty chemicals market. The reaction is general for hydrocarbons containing olefinic bonds. The reaction was originally referred to as disproportionation. The more appropriate name "metathesis" was introduced in 1967 and is now commonly used.

Metathesis can be visualized as a net breaking and reformation of two olefinic carbon-carbon bonds. A generalized metathesis reaction can be represented as follows:

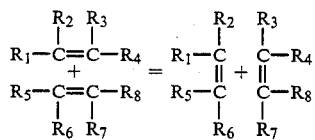

Each of $R_1$, $R_2$, $R_3$, $R_4$, $R_5$, $R_6$, $R_7$ and $R_8$ is independently representative of hydrogen or a hydrocarbon group. A simple but commercially significant example of the reaction is the conversion of propylene to ethylene and normal butenes.

Olefin metathesis reactions are presently believed to proceed through a single-step metallocarbene scheme involving a metallocyclobutane intermediate as illustrated below:

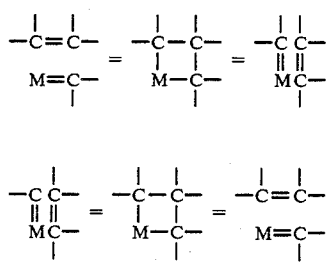

where M is W, Mo or Re catalytic sites. Support for the validity of this generally accepted mechanism has been provided by very detailed kinetic and mechanistic studies conducted by several groups of investigators. However, for predicting primary products of industrial metathesis applications, the simple "four-center" or "quasi-cyclobutane" concerted mechanism shown below is adequate and more direct:

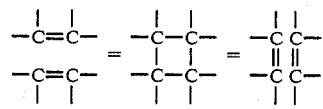

As depicted in both schemes, the types and total number of bonds remain unchanged; as a result, metathesis reactions are essentially thermoneutral. Another characteristic of the metathesis reaction is that the integrity of the alkylidene moieties is retained during transformation.

Metathesis reactions of acyclic mono-olefins can be classified into two groups: (1) self-metathesis of a single olefin and (2) cross-metathesis of double-bond isomers or of two different olefins. In the first case, two primary metathesis products are produced, e.g., propylene yields ethylene and 2-butene. In the second case, sets of both self- and cross-metathesis products are obtained. For example, the metathesis of a 1-pentene/2-pentene mixture yields the following sets: ethylene/4-octene, propylene/3-heptene, 1-butene/2-hexene, and 2-butene/3-hexene. When ethylene is one of the reactants, alpha-olefins are produced as a consequence of "ethylene cleavage". For example, ethylene cleavage of 3-hexene yields 1-butene. Cross-metathesis of acyclic olefin/cyclic olefin mixtures yields diolefins. For example, ethylene cleavage of cyclic olefins provides a new route for the production of alpha, omega-diolefins as illustrated below:

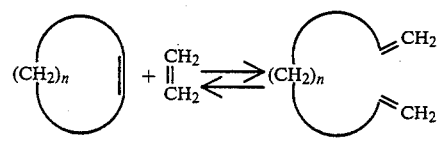

The metathesis of other types of olefins and olefin mixtures, including diolefins, ring-substituted olefins (e.g., styrene), and functionally-substituted olefins produces products consistent with the above schemes. In theory, the number of olefin metathesis reactions is limited only by the number of compounds containing carbon-carbon double bonds. Metathesis reactions include, but are not limited to, the following:

(1) The metathesis of an acyclic mono- or polyene having at least three carbon atoms into other mono- or polyenes of both higher and lower number of carbon atoms; for example, the disproportionation of propylene yields ethylene and butenes; the disproportionation of 1,5-hexadiene yields ethylene and 1,5,9-decatriene;

(2) The reaction of an acyclic mono- or polyene having three or more carbon atoms and a different acyclic mono- or polyene having three or more carbon atoms to produce different acyclic olefins; for example, the reaction of propylene and isobutylene yields ethylene and isopentene;

(3) The reaction of ethylene and an internal acyclic mono- or polyene having four or more carbon atoms to produce other olefins having a lower number of carbon atoms than that of the acyclic mono- or polyenes; for example, the reaction of ethylene and 4-methylpentene-2 yields 3-methylbutene-1 and propylene;

(4) The reaction of ethylene or an acyclic mono- or polyene having three or more carbon atoms with a cyclic mono- or cyclic polyene to produce an acyclic polyene having a higher number of carbon atoms than that of any of the starting materials; for example, the reaction of cyclooctene and 2-butene yields 2,10-dodecadiene; the reaction of 1,5-cyclooctadiene and ethylene yields 1,5,9-decatriene;

(5) The reaction of one or more cyclic mono- or cyclic polyenes to produce a cyclic polyene having a higher number of carbon atoms than any of the starting materials; for example, the reaction of cyclooctene yields cyclohexadecadiene;

(6) The reaction conversion of an acyclic polyene having at least 7 carbon atoms and having at least 5 carbon atoms between any two double bonds to produce acyclic and cyclic mono- and polyenes having a lower number of carbon atoms than that of the feed; for example, the reaction of 1,7-octadiene yields cyclohexene and ethylene; or (7) The reaction of one or more acyclic polyenes having at least three carbon atoms between any two double bonds to produce acyclic and cyclic mono- and polyenes generally having both a higher and lower number of carbon atoms than that of the feed material; for example, the reaction of 1,4-pentadiene yields 1,4-cyclohexadiene and ethylene.

In addition to olefinic reactants the metathesis reaction can successfully proceed with acetylenic reactants. For example, the metathesis of 2-pentyne yields 2-butyne and 3-hexyne.

Metathesis catalysts include both homogeneous and heterogeneous catalysts. Based on current commercial activity the heterogeneous catalyst appears to have the greatest utility. Among the most effective metathesis catalysts are the oxides of molybdenum, tungsten and rhenium supported on a high surface area alumina or silica. Typical compositions and physical properties of three such metal oxide catalysts are given below in Table I.

TABLE I

Typical Compositions, Physical Properties and Reaction Temperatures of Three Common Heterogeneous Metathesis Catalysts

|  | $CoO.MoO_3.Al_2O_3$ | $WO_3.SiO_2$ | $Re_2O_7.Al_2O_3$ |
|---|---|---|---|
| Composition, Wt % |  |  |  |
| $MoO_3$ | 11.0 |  |  |
| $WO_3$ |  | 6.8 |  |
| $Re_2O_7$ |  |  | 14 |
| CoO | 3.4 |  |  |
| $Al_2O_3$ | 85.6 | <0.1 | 86 |
| $SiO_2$ |  | 93.2 |  |
| Physical Properties |  |  |  |
| Surface Areas, $m^2/g$ | 285 | 345 | 255 |
| Pore Volume, cc/g | 0.58 | 0.98 | 0.37 |
| Avg. Pore Diameter, Å | 82 | 114 | 58 |
| Reaction Temp., °C. | 100–200 | 300–500 | 0–100 |

Molybdenum oxide-alumina and cobalt molybdate-alumina catalysts are readily and commercially available for metathesis applications. These catalysts exhibit their best metathesis activity in the 100°–200° C. temperature range.

Tungsten oxide-silica is a commercially available catalyst developed specifically for metathesis by the Phillips Petroleum Company. This catalyst is best suited for metathesis in the 300°–500° C. temperature range. It is less susceptible to trace quantities of catalyst poisons in the feed stream than are the lower temperature alumina-based catalysts.

The rhenium oxide-alumina catalyst is active for metathesis at ambient conditions. It can be prepared in the laboratory in accordance with a variety of techniques including the impregnation of high surface area alumina with aqueous ammonium perrhenate solutions.

Other combinations of the oxides and the supports can be successfully employed.

For more information concerning metathesis the reader is advised to seek out and read the following references:

1. G. C. Bailey (1969) "Catalysis Reviews" Vol. 3, pages 37–60.

2. R. L. Banks (1981) "Specialist Periodical Reports", Vol. 4, pages 100–129.

3. R. L. Banks (1979) "Chemtech" Vol. 9, pages 494–500.

Persons of skill in the art of olefin (and acetylenic) metathesis seek to improve (i.e. increase) the conversion of reactants to products. The selection of catalyst is an important factor. Accordingly, it is one object of this invention to provide a metathesis process of improved conversion. It is also an object of this invention to provide catalysts of improved utility including increased metathesis conversion.

Broadly, it is an object of this invention to provide a novel composition of matter.

It is a further object of this invention to provide a novel metathesis process.

These objects and other objects and advantages of this invention will become apparent to persons of skill in the art of metathesis upon reading this disclosure and the appended claims.

BRIEF SUMMARY OF THE INVENTION

The composition of this invention is broadly represented by the combination of (a) supported tungsten oxide, supported molybdenum oxide, or a mixture thereof and (b) elemental tungsten, silicon, antimony, or any mixture of 2 or more thereof. In accordance with one aspect of this invention the composition can be described as a supported tungsten oxide or supported molybdenum oxide catalyst (or mixture thereof) treated with elemental tungsten, silicon or antimony (or mixture thereof). The treated catalyst is useful for catalytic purposes in the metathesis of olefinic and acetylenic compounds. This invention includes the process of metathesis in the presence of the above-described treated catalyst.

This invention is defined further and more completely by the disclosure which follows.

DETAILED DESCRIPTION OF THE INVENTION

The novel composition of this invention is a combination of components including (a) supported tungsten oxide or supported molybdenum oxide (or mixture thereof) and (b) elemental tungsten, silicon or antimony (or mixture thereof). In accordance with one aspect of this invention the composition can be described as a supported tungsten oxide or supported molybdenum oxide (or mixture thereof) catalyst treated with a treating agent selected from elemental tungsten, elemental silicon and elemental antimony (or mixture thereof).

The process of this invention can be briefly described as the metathesis of olefinic or acetylenic compounds in the presence of the above-described treated catalyst.

The tungsten and molybdenum oxides of this invention include any of the oxides of tungsten and molybdenum. A number of oxidation states are known and include, but are not limited to, the trioxides (e.g., $WO_3$ and $MoO_3$), the dioxides (e.g., $WO_2$ and $MoO_2$) and intermediate oxides (e.g., $Mo_2O_5$). The invention includes the use of mixtures of different oxidation states of tungsten oxide and molybdenum oxide as well as tungsten oxide and molybdenum oxide.

The tungsten oxide or molybdenum oxide is combined with a support (or catalyst carrier). Suitable supports include, but are not limited to, oxides of Al, Si, Fe, Ni, Zr, Sn, Th, SiAl, AlTi, AlTh, MgSi and MgTi and phosphates of Al, Ti, Ca, Zr and Mg. Other supports recognized as suitable by those of skill in the art and suitable supports yet to be discovered are intended to be included within the scope of this invention. These supports are believed to contribute to the catalytic utility of the tungsten oxide or molybdenum oxide. Alumina and silica are the best of the known supports. These supports are preferred because of the high catalytic activity of the resulting catalyst composition and because of their ready availability and stability. Further information concerning catalyst supports or carriers in general can be found in numerous sources of information available in the relevant literature such as, for example, the "Encyclopedia of Chemical Processing and Design", Marcel Dekker, Inc., Vol. 7, pages 1–19.

Many methods can be used to produce the supported tungsten oxide or supported molybdenum oxide. In accordance with one such method, anhydrous tungstic acid ($H_2WO_4$) and silica gel are mulled together in, for example, a mixing extruder to produce a mixture that is heated to drive off water. The mixture can be contacted with a flowing gas stream (e.g., an inert gas such as $N_2$) to aid water removal. In accordance with another method, silica gel is impregnated with ammonium metatungstate (($NH_4)_2W_4O_{13}\cdot 8H_2O$) to produce a material that is heated in the presence of an oxidizing gas (e.g., $O_2$, air). The oxidizing gas can be a flowing gas. The material is subsequently flushed with a flowing inert gas (e.g., $N_2$) stream. The purpose of the heat treatment is threefold: (1) to convert the tungsten to tungsten oxide; (2) to facilitate interaction between the tungsten oxide and the silica; and (3) to remove water and other polar compounds. The heating temperature should be high enough to accomplish these objectives. A temperature of at least 400° C. is usually required for satisfactory results. Good results can be obtained within the 500°–700° C. temperature range. Excessively high temperatures should be avoided to prevent catalyst sintering. The heat treatment should usually last about 0.1 to about 20 hours or longer.

Molybdenum oxide supported on alumina or silica can be prepared in accordance with methods similar to the above-described methods. Anhydrous molybdic acid ($H_2MoO_4$) can be employed in place of tungstic acid or ammonium molybdate (($NH_4)_2MoO_4$) or ammonium paramolybdate (($NH_4)_6Mo_7O_{24}\cdot 4H_2O$) employed in place of ammonium metatungstate.

Persons skilled in the relevant art possess the requisite knowledge and ability to produce numerous other supported tungsten and molybdenum oxides. Given the large number of suitable supports it would be inappropriate to burden this disclosure with a myriad of detailed descriptions. More properly, attention should be focused on the essence of this invention which is the concept of treating supported tungsten oxide or supported molybdenum oxide with elemental tungsten, silicon or antimony.

The treating agent of this invention is selected from elemental tungsten, elemental silicon and elemental antimony. These elements are commercially available. Furthermore, techniques for the recovery of these elements from naturally occurring sources are well known.

In accordance with this invention the supported tungsten oxide or supported molybdenum oxide is treated with the treating agent by combining the supported oxide with the treating agent or by otherwise bringing the treating agent into close proximity with the supported oxide. This can be done, for example, by mixing particulates (e.g., particles, granules, pellets or the like) of the supported tungsten (or molybdenum) oxide with particulates (e.g., particles, granules, pellets or the like) of the treating agent. In another example, the treating agent, in the form of a powder, is sprinkled on or mixed with the supported tungsten (or molybdenum) oxide. In yet another example the treating agent can be melted and dropped onto the catalyst. In a final example a stream of inert gas (e.g., nitrogen or argon) can be passed through molten treating agent and then into contact with the supported tungsten (or molybdenum) oxide. It should be noted that only antimony has a melting point sufficiently low to make the latter two procedures practicable. Other methods for combining the supported tungsten (or molybdenum) oxide and treating agent exist and are within the scope of this invention.

The combination of supported tungsten (or molybdenum) oxide and treating agent is preferably activated by heating in an inert gas (e.g., nitrogen, argon, etc.). A flowing inert gas can be used. It is believed that the inert gas aids removal of deactivating impurities (such as oxygen) from the system. The activation temperature should generally be at least about 400° C. Good results have been obtained using a 600°–700° C. temperature range. Excessively high temperatures should be avoided to prevent catalyst sintering. The duration of the activation period can vary widely. We have obtained good results by operating within a 10 minute to 120 minute range. Others may desire to use an activation period as short as 1 minute or up to about 10 hours or longer.

In addition to the tungsten oxide or molybdenum oxide the composition can contain other compounds in oxide or other forms. For example, an alumina-supported $MoO_3$ can further contain CoO. These other compounds are optional. In other words the presence of other compounds in the composition does not remove it from the scope of this invention.

This invention and the appended claims also include compositions which are mixtures of supported tungsten oxide and supported molybdenum oxide and treating agents which are mixtures of at least two of elemental tungsten, silicon and antimony.

The composition of this invention is broadly defined to encompass any combination of (a) supported tungsten oxide or supported molybdenum oxide and (b) a treating agent selected from elemental tungsten, silicon and antimony. Although this invention is not limited thereto it is contemplated that the weight percentages of the components of the composition will generally be within the ranges provided below:

|  | Broad Range | Preferred Range |
| --- | --- | --- |
| tungsten oxide (and/or molybdenum oxide) | 0.1 to 50 wt % | 1 to 15 wt % |
| treating agent(s) | 0.1 to 30 wt % | 1 to 15 wt % |
| support | (balance) | (balance) |

The above weight percentages are based upon the total weight of tungsten oxide (or molybdenum oxide) support and treating agent. When a mixture of tungsten oxide and molybdenum oxide or a mixture of treating agents is used in the composition the above ranges apply to the total amount of tungsten oxide and molybdenum oxide or to the total amount of treating agents. The preferred ranges are preferred because optimum conversion is obtained with the most efficient use of catalytic materials.

Although the weight ratio of tungsten oxide (or molybdenum oxide) to treating agent can vary widely it is contemplated that this weight ratio will usually be within the range of about 10:1 to about 1:4. This invention, as broadly defined, is not limited to the above range however.

This invention includes a process, that is, the metathesis of a feed in the presence of the composition of this invention.

The inventive composition can be used in metathesis reactions in a conventional manner. The reaction temperature can vary depending upon the type of support, metal oxide and treating agent employed, the particular feed, reaction pressure, contact time, etc. Typically, the metathesis is carried out at a temperature in the range of about 0° to about 600° C., preferably about 100° to about 500° C. Generally, a temperature in the range of about 100° to 300° C. is preferred when an alumina support is employed and about 200° to 500° C. when a silica support is employed. The pressure during the metathesis reaction may vary between wide limits. Pressures between 0.1 and 500 atm. are suitable; recommended pressures are between 1 and 40 atm. The process of this invention is not limited to any specific temperature or pressure ranges and requires only that conditions be sufficient to allow metathesis to proceed.

The metathesis reaction can be carried out by contacting the feed, in either gas or liquid phase, with the catalyst. Whether the feed is in the liquid phase or the gas phase will depend on the structure and molecular weight of the feed and on reaction conditions such as temperature and pressure.

If the reaction is carried out in the liquid phase, solvents or diluents for the reactants may be used. Saturated aliphatic hydrocarbons (e.g. pentane, hexane, cyclohexane, dodecane) and aromatic hydrocarbons such as benzene and toluene are suitable. If the reaction is carried out in the gaseous phase, diluents such as aliphatic hydrocarbons (e.g., methane, ethane, propane and/or substantially inert gases (e.g., nitrogen) may be present. Preferably the reaction is effected in the absence of significant amounts of deactivating materials such as water and oxygen.

Although the length of time during which the feed is contacted with the composition is not believed to be critical, it may vary between 0.1 seconds and 24 hours. Longer and shorter contact times may be used. The contact time needed to obtain a reasonable yield of products depends on several factors such as the activity of the catalyst, temperature, pressure and structure of the reactants. It should be noted that too long a contact time results in undesirable side reactions which lead to poor selectivity to desired products.

The process of the invention can be effected batchwise or continuously; with fixed catalyst beds, slurried catalysts, fluidized catalyst beds or by using any other conventional contacting techniques. The solid catalysts can be applied in any appropriate form, for example, as powders, flakes, pellets, spheres, extrudates or the like.

The feed must contain reactants that are characterized by either olefinic unsaturation (i.e. C=C) or acetylenic unsaturation (i.e. C≡C). In most applications the reactants will be unsaturated hydrocarbons. This includes acyclic and cyclic monoolefins, diolefins, acetylenes and the like. The process also includes organic reactants having, in addition to the above-described unsaturation, other functional groups

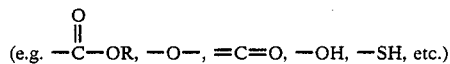

All that is required is that the reactants be susceptible to the metathesis reaction.

After extended use of the promoted catalyst in the metathesis process it is desirable to regenerate the promoted catalyst. This can be accomplished by treating the catalyst with flowing oxygen or air at about 400° to about 700° C. for about 10 minutes to about 20 hours. The regeneration should be concluded with an inert gas (e.g., $N_2$) flush under the same conditions.

THE EXAMPLES

The following examples are provided to better illustrate this invention and to demonstrate the increased conversion obtained through practice of the invention. More specifically it is shown that the catalytic utility of a tungsten oxide on silica metathesis catalyst is improved by the addition of elemental W (tungsten), Si (silicon) or Sb (antimony).

In each example the tungsten oxide content of the catalyst was 6 weight percent based on the total weight of tungsten oxide and silica. The catalysts were prepared by impregnating high surface area silica with 0.0727 gram of ammonium metatungstate $((NH_4)_2W_4O_{13} \cdot 8H_2O)$ per gram of silica. The impregnation was accomplished by treating the silica with an aqueous solution of the ammonium metatungstate. The impregnated silica was dried and calcined in air at 500° C. to convert the metatungstate to the oxide. A $-20+40$ mesh sieve fraction was obtained for use as described below.

All runs were made by passing a propylene feed through a vertical tubular quartz reactor (1 cm in diameter and 25 cm in length) positioned in a temperature-controlled electric furnace. In each run the reactor contained a bed of the designated catalyst. A thermocouple was positioned in the catalyst bed to monitor reaction temperature. Prior to each run the catalyst was activated by heating at 600° C. in flowing nitrogen for 0.5 hour. Regeneration, when indicated, was accomplished with flowing air at 600° C. for one hour, followed by a nitrogen flush at 600° C. The propylene feed was of a polymerization grade as sold by Phillips Petroleum Company of Bartlesville, Okla. The propylene feed was pretreated with activated Alcoa H151 alumina and activated magnesia prior to metathesis. The feed was passed downwardly through the vertically oriented tubular reactor. Reaction product analyses were made by gas-liquid chromatography (GLC) employing a Hewlett-Packard model 5880A chromatograph having a ⅛ inch by 20 ft. column packed with 19% BMEE+1% squalene on 60/80 Chrom P. Analysis was carried out isothermally at a temperature of about 30° to 40° C. with a helium carrier gas flow rate of about 20 mL/min.

EXAMPLE I

In this example silica-supported tungsten oxide treated with elemental tungsten is compared to untreated silica-supported tungsten oxide. In each run 1.5 grams of silica-supported tungsten oxide was employed in the reactor. The elemental tungsten, when used, was added as a power (−100 mesh size) by pouring it onto the top of the silica-supported tungsten oxide bed. In runs II and III, 0.1 and 0.2 gram, respectively, of the elemental tungsten powder were used. The concentration of elemental tungsten in each run is given in Table I.

Following activation (or regeneration) and during the metathesis the catalyst bed was maintained at a temperature of 460° C. The propylene feed was continuously fed to the reactor at a rate of 120 mL/min. Table I, below, shows propylene conversion to ethylene and n-butenes at various times on stream. Selectivity to these products was essentially quantitative.

TABLE I

| Run | Catalyst | Mole % Conversion of $C_3H_6$ at | | | |
|-----|----------|--------|--------|--------|--------|
|     |          | 15 min | 30 min | 60 min | 90 min |
| I   | silica-supported tungsten oxide only | 11.4 | 16.2 | 21.0 | 23 |
| II  | silica-supported tungsten oxide + 6.3 wt % W | 37.1 | 42.3 | 43.3 | 44 |
| III | silica-supported tungsten oxide + 11.8 wt % W | 36.9 | 39.9 | 41.8 | 43 |
| IV  | III after regeneration | 13.9 | 19.7 | 24.3 | 26 |
| V   | IV after regeneration | 14.1 | 20.4 | 25 | — |

Runs II and III, which illustrate one embodiment of this invention, show the increased metathesis conversion resulting from the addition of powdered tungsten metal to silica-supported tungsten oxide. Runs IV and V show that after regeneration the catalyst was still more active than the catalyst of run I.

EXAMPLE II

In this example silica-supported tungsten oxide treated with elemental silicon is compared to untreated silica-supported tungsten oxide. The elemental silicon was added to the silica-supported tungsten oxide as a fine powder by preliminary admixture of 0.07 grams of the powder with the silica-supported tungsten oxide prior to charging of the reactor with the catalyst. The concentration of elemental silicon in the catalyst mixture was 4.2 weight percent based upon the total weight of silica in the catalyst mixture (i.e., $WO_3 \cdot SiO_2$ plus Si).

In each run about 1.5 to 1.6 grams of the designated catalyst was employed in the reactor. Following activation (or regeneration) and during the metathesis the catalyst bed was maintained at a temperature of 400° C. The propylene feed was continuously fed to the reactor at a rate of 150 mL/min. Table II, below, gives propylene conversion to ethylene and n-butenes at various times on stream. Selectivity to these products was essentially quantitative.

TABLE II

| Run | Catalyst | Mole % Conversion of $C_3H_6$ at | | | | | |
|-----|----------|--------|--------|--------|--------|---------|---------|
|     |          | 27 min | 48 min | 68 min | 90 min | 132 min | 153 min |
| I    | silica-supported tungsten oxide only | — | 20.4 | — | 20.8 | 21.0 | — |
| II   | silica-supported tungsten oxide only | 6.8 | 8.2 | 8.8 | 9.0 | 8.9 | — |
| III  | silica-supported tungsten oxide only | 18.4 | 17.3 | 16.0 | 14.9 | 13.9 | 13.3 |
| IV   | III after regeneration | 15.2 | 14.6 | 14.2 | 13.7 | — | — |
| V    | silica-supported tungsten oxide + 4.2 Wt % Si | 48.4 | 48.1 | 48.7 | 47.6 | 47.1 | 46.9 |
| VI   | V after regeneration | 48.1 | 47.8 | — | — | 46.8 | 46.1 |
| VII  | VI after regeneration | 47.9 | 47.6 | 47.3 | 46.0 | 45.5 | 45.3 |
| VIII | VII after regeneration | 29.7 | 32.5 | 33.6 | 34.5 | 34.8 | 35.2 |

Runs I–IV were made without treatment with elemental silicon and provide a basis for comparison of inventive runs V–VIII. Runs I, II, and III were made with fresh portions of catalyst; run IV was made with the same catalyst that was used in run III after regeneration. Runs V–VIII were all made with the same catalyst with intervening periods of oxidative regeneration. The data show significantly improved metathesis conversion with the silicon treatment.

EXAMPLE III

In this example silica-supported tungsten oxide treated with elemental antimony is compared to untreated silica-supported tungsten oxide. In each run 1.8 grams of the silica-supported tungsten oxide was employed in the reactor. The elemental antimony, when used, was added as a fine powder by pouring 0.03 gram of the powder onto the top of the silica-supported tungsten oxide bed. The concentration of elemental antimony was 1.6 weight percent based upon the total amount of tungsten oxide, silica and antimony.

Following activation (or regeneration) and during the metathesis the catalyst bed was maintained at a temperature of 420° C. The propylene feed was continuously fed to the reactor at a rate of 100 mL/min. Table III, below, gives propylene conversion to ethylene and n-butenes at various times on stream. Selectivity to these products was essentially quantitative.

TABLE III

| Run | Catalyst | Mole % Conversion of $C_3H_6$ at | | | | |
|-----|----------|--------|--------|--------|--------|---------|
|     |          | 25 min | 46 min | 67 min | 88 min | 109 min |
| I   | silica-supported tungsten oxide only | 15.6 | 18.1 | 20.1 | 21.3 | 22.2 |
| II  | I + 1.6% wt % Sb | 30.8 | 32.6 | 33.2 | 33.1 | 32.9 |
| III | II after regeneration | 23.1 | 24.9 | 27.3 | 27.5 | 27.1 |

The catalyst in run II was the catalyst of run I treated with powdered antimony. The data show significantly improved metathesis conversion with the antimony treatment.

We claim:
1. A composition comprising:

(a) an oxide selected from the group consisting of tungsten oxide, molybdenum oxide and a mixture thereof,
(b) a support, and
(c) an element selected from the group consisting of tungsten, silicon, antimony and any mixture of 2 or more thereof when (a) is tungsten oxide or a mixture of tungsten oxide and molybdenum oxide or an element selected from the group consisting of tungsten, silicon, a mixture of tungsten and silicon, a mixture of antimony and tungsten, a mixture of antimony and silicon and a mixture of antimony, tungsten and silicon when (a) is molybdenum oxide;
wherein (a) is supported by (b).

2. A composition according to claim 1 wherein said support is selected from the group consisting of oxides of Al, Si, Fe, Ni, Zr, Sn, Th, SiAl, AlTi, AlTh, MgSi and MgTi and phosphates of Al, Ti, Ca, Zr and Mg, and mixtures of any 2 or more thereof.

3. A composition according to claim 1 wherein said support comprises alumina.

4. A composition according to claim 1 wherein said support comprises silica.

5. A catalyst comprising supported tungsten oxide treated with a treating agent; wherein said treating agent is an element selected from the group consisting of tungsten, silicon, antimony and any mixture of 2 or more thereof.

6. A catalyst according to claim 5 wherein said tungsten oxide is supported by a support selected from the oxides of Al, Si, Fe, Ni, Zr, Sn, Th, SiAl, AlTi, AlTh, MgSi and MgTi, phosphates of Al, Ti, Ca, Zr and Mg and any mixture of 2 or more thereof.

7. A catalyst according to claim 5 wherein said tungsten oxide is supported by alumina.

8. A catalyst according to claim 5 wherein said tungsten oxide is supported by silica.

9. A catalyst according to claim 5 wherein said supported tungsten oxide is in the form of particulates; wherein said treating agent is in the form of particulates; and wherein said supported tungsten oxide and said treating agent are mixed together.

10. A catalyst according to claim 5 wherein said treating agent is in the form of a powder, and wherein said treating agent is sprinkled on or mixed with said supported tungsten oxide.

11. A catalyst according to claim 5 that has been activated by heating in an inert gas.

12. A catalyst according to claim 11 wherein said catalyst is heated at a temperature of at least about 400° C.

13. A catalyst according to claim 11 wherein said catalyst is heated at a temperature of about 600° to 700° C.; and wherein said gas is flowing.

14. A catalyst according to claim 6 wherein the amount of tungsten oxide ranges from about 0.1 to about 50 weight percent; wherein the amount of said treating agent ranges from about 0.1 to about 30 weight percent; and wherein said weight percentages are based upon the total weight of said support, said tungsten oxide and said treating agent.

15. A catalyst according to claim 6 wherein the amount of tungsten oxide ranges from about 1 to about 15 weight percent; wherein the amount of treating agent ranges from about 1 to about 15 weight percent; and wherein said weight percentages are based upon the total weight of said support, said tungsten oxide and said treating agent.

16. A catalyst comprising supported molybdenum oxide treated with a treating agent; wherein said treating agent is an element selected from the group consisting of tungsten and silicon, a mixture of tungsten and silicon, a mixture of antimony and tungsten, a mixture of antimony and silicon, and a mixture of antimony, tungsten and silicon.

17. A catalyst according to claim 16 wherein said molybdenum oxide is supported by a support selected from the oxides of Al, Si, Fe, Ni, Zr, Sn, Th, SiAl, AlTi, AlTh, MgSi and MgTi, phosphates of Al, Ti, Ca, Zr and Mg, and any mixture of 2 or more thereof.

18. A catalyst according to claim 16 wherein said molybdenum oxide is supported by alumina.

19. A catalyst according to claim 16 wherein said molybdenum oxide is supported by silica.

20. A catalyst according to claim 16 wherein said supported molybdenum oxide is in the form of particulates; wherein said treating agent is in the form of particulates; and wherein said supported molybdenum oxide and said treating agent are mixed together.

21. A catalyst according to claim 16 wherein said treating agent is in the form of a powder, and wherein said treating agent is sprinkled on or mixed with said supported molybdenum oxide.

22. A catalyst according to claim 16 that has been activated by heating in an inert gas.

23. A catalyst according to claim 22 wherein said catalyst is heated at a temperature of at least about 400° C.

24. A catalyst according to claim 22 wherein said catalyst is heated at a temperature of about 600° to 700° C.; and wherein said gas is flowing.

25. A catalyst according to claim 17 wherein the amount of molybdenum oxide ranges from about 0.1 to about 50 weight percent; wherein the amount of said treating agent ranges from about 0.1 to about 30 weight percent; and wherein said weight percentages are based upon the total weight of said support, said molybdenum oxide and said treating agent.

26. A catalyst according to claim 17 wherein the amount of molybdenum oxide ranges from about 1 to about 15 weight percent; wherein the amount of treating agent ranges from about 1 to about 15 weight percent; and wherein said weight percentages are based upon the total weight of said support, said molybdenum oxide and said treating agent.

27. The composition produced in accordance with a method comprising
(i) mulling together anhydrous tungstic acid and silica gel to produce a mixture,
(ii) heating said mixture to drive off water,
(iii) treating said mixture with an element selected from the group consisting of tungsten, silicon, antimony, and mixtures of any two or more thereof, and
(iv) activating said treated mixture by heating in an inert gas at a temperature of at least about 400° C.

28. The composition of claim 27 wherein said mixture is contacted with a flowing gas stream to aid water removal prior to step (iii).

29. The composition produced in accordance with a method comprising
(i) impregnating silica gel with ammonium metatungstate, (ii) heating said impregnated silica gel in the presence of an oxidizing gas, (iii) treating said impregnated silica gel with a treating agent selected from the group consisting of tungsten, silicon, antimony, and mixtures of any 2 or more thereof, and (iv) activating said treated impregnated silica gel by heating in an inert gas at a temperature of at least about 400° C.

30. The composition of claim 29 wherein said oxidizing gas is a flowing gas.

31. The composition of claim 29 wherein said impregnated silica gel is flushed with an inert gas after step (ii) but prior to step (iii).

32. The composition produced in accordance with a method comprising (i) mulling together anhydrous molybdic acid and silica gel to produce a mixture, (ii) heating said mixture to drive off water, (iii) treating said mixture with a treating agent selected from the group consisting of tungsten and silicon and a mixture thereof, and (iv) activating said treated mixture by heating in an inert gas at a temperature of at least about 400° C.

33. The composition of claim 32 wherein said mixture is contacted with a flowing gas stream to aid water removal prior to step (iii).

34. The composition produced in accordance with a method comprising (i) impregnating silica gel with ammonium molybdate or ammonium paramolybdate, (ii) heating said impregnated silica gel in the presence of an oxidizing gas, (iii) treating said impregnated silica gel with a treating agent selected from tungsten and silicon and a mixture thereof, and (iv) activating said treated impregnated silica gel by heating in an inert gas at a temperature of at least about 400° C.

35. The composition of claim 34 wherein said oxidizing gas is a flowing gas.

36. The composition of claim 34 wherein said impregnated silica gel is flushed with an inert gas after step (ii) but prior to step (iii).

* * * * *